(12) United States Patent
Nitsche et al.

(10) Patent No.: US 10,794,824 B2
(45) Date of Patent: Oct. 6, 2020

(54) SYSTEMS AND METHODS FOR TERAHERTZ SPECTROSCOPY

(71) Applicant: HALLIBURTON ENERGY SERVICES, INC., Houston, TX (US)

(72) Inventors: Wolfgang Hartmut Nitsche, Humble, TX (US); Michael T. Pelletier, Houston, TX (US); John Laureto Maida, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 148 days.

(21) Appl. No.: 16/313,585

(22) PCT Filed: Sep. 30, 2016

(86) PCT No.: PCT/US2016/054891
§ 371 (c)(1),
(2) Date: Dec. 27, 2018

(87) PCT Pub. No.: WO2018/063364
PCT Pub. Date: Apr. 5, 2018

(65) Prior Publication Data
US 2019/0323957 A1 Oct. 24, 2019

(51) Int. Cl.
G01J 5/02 (2006.01)
G01N 21/3581 (2014.01)
E21B 49/08 (2006.01)
G01N 33/28 (2006.01)

(52) U.S. Cl.
CPC ....... *G01N 21/3581* (2013.01); *E21B 49/081* (2013.01); *G01N 33/2823* (2013.01); *E21B 49/0875* (2020.05); *G01N 2201/08* (2013.01)

(58) Field of Classification Search
CPC . E21B 49/003; E21B 49/081; G01N 21/3581; G01N 33/2823; G01N 2201/08; G01N 33/241; G01N 2021/3595; G06N 5/046; G06F 15/18
See application file for complete search history.

(56) References Cited

U.S. PATENT DOCUMENTS

| | | | |
|---|---|---|---|
| 6,479,822 B1 | 11/2002 | Nelson et al. | |
| 8,969,804 B2 | 3/2015 | Tripodi et al. | |
| 9,234,835 B2 | 1/2016 | Pelletier et al. | |
| 2008/0319293 A1 | 12/2008 | Looney et al. | |

(Continued)

OTHER PUBLICATIONS

International Search Report and Written Opinion dated May 10, 2017, for PCT/US2016/054891 filed on Sep. 30, 2016.

*Primary Examiner* — Don K Wong
(74) *Attorney, Agent, or Firm* — Chamberlain Hrdlicka

(57) ABSTRACT

A method, system, and device for terahertz spectroscopy to analyze a sample. The device comprises a transmitter, a waveguide, a receiver, and a processor. The transmitter generates electromagnetic (EM) radiation in a terahertz frequency band from about 0.1 terahertz to about 10 terahertz. The waveguide propagates the EM radiation generated from the transmitter and houses the sample to attenuate the EM radiation. The receiver is in communication with the waveguide and generates a signal in response to EM radiation propagating in the waveguide. The processor analyzes the signal to identify a parameter associated with the sample.

24 Claims, 5 Drawing Sheets

(56) References Cited

U.S. PATENT DOCUMENTS

| | | | |
|---|---|---|---|
| 2010/0314545 A1* | 12/2010 | Logan, Jr. | ............ G01J 3/10 250/339.07 |
| 2012/0250017 A1 | 10/2012 | Morys et al. | |
| 2015/0086152 A1 | 3/2015 | Samson et al. | |

* cited by examiner

SYSTEMS AND METHODS FOR TERAHERTZ SPECTROSCOPY

This section is intended to provide relevant contextual information to facilitate a better understanding of the various aspects of the described embodiments. Accordingly, it should be understood that these statements are to be read in this light and not as admissions of prior art.

In the oil industry, precipitation of asphaltenes can cause various problems throughout a production system, from near wellbore reservoir to production tubing, flowlines, and processing facilities, e.g., separators. Asphaltene deposits can reduce permeability in reservoirs, decrease production rates in production tubing, restrict flowlines, collect in separators, and can stabilize emulsions between oil and water.

Spectroscopy systems are used to analyze a sample based on its interaction with frequency components of electromagnetic (EM) radiation. For example, optical spectroscopy is an analytical technique that derives information about a sample being evaluated by the interaction of that sample with light in the ultraviolet (UV) to infrared (IR) range of wavelengths. The interaction changes the properties of the light, for example, the frequency (color), intensity, polarization, or direction (scattering or refraction). However, optical spectroscopy cannot provide information about large asphaltenes, such as nanocolloidally dispersed asphaltenes that have molecular structures with at least 100 carbon atoms.

EM radiation in a terahertz frequency band offers another spectrum to provide information about samples not able to be analyzed using other spectrums. As used herein, EM radiation in a terahertz frequency band includes a frequency range from about 0.1 terahertz to about 10 terahertz. As described herein, about 0.1 terahertz refers to ±10% of 0.1 terahertz, and about 10 terahertz refers to ±10% of 10 terahertz. However, existing terahertz spectroscopy systems are not sensitive to samples that have a weak interaction with terahertz EM radiation, such as asphaltenes. This disclosure provides a terahertz spectroscopy system that is responsive to weak interactions between a sample and EM radiation in the terahertz frequency band.

DESCRIPTION OF THE DRAWINGS

For a detailed description of the embodiments, reference will now be made to the accompanying drawings in which.

DETAILED DESCRIPTION

This disclosure provides an electromagnetic spectroscopy system and methods of use. Specifically, the disclosure provides a spectroscopy system that is sensitive to weak spectral signals encountered between a sample and EM radiation in the terahertz frequency band.

Figure 1A:
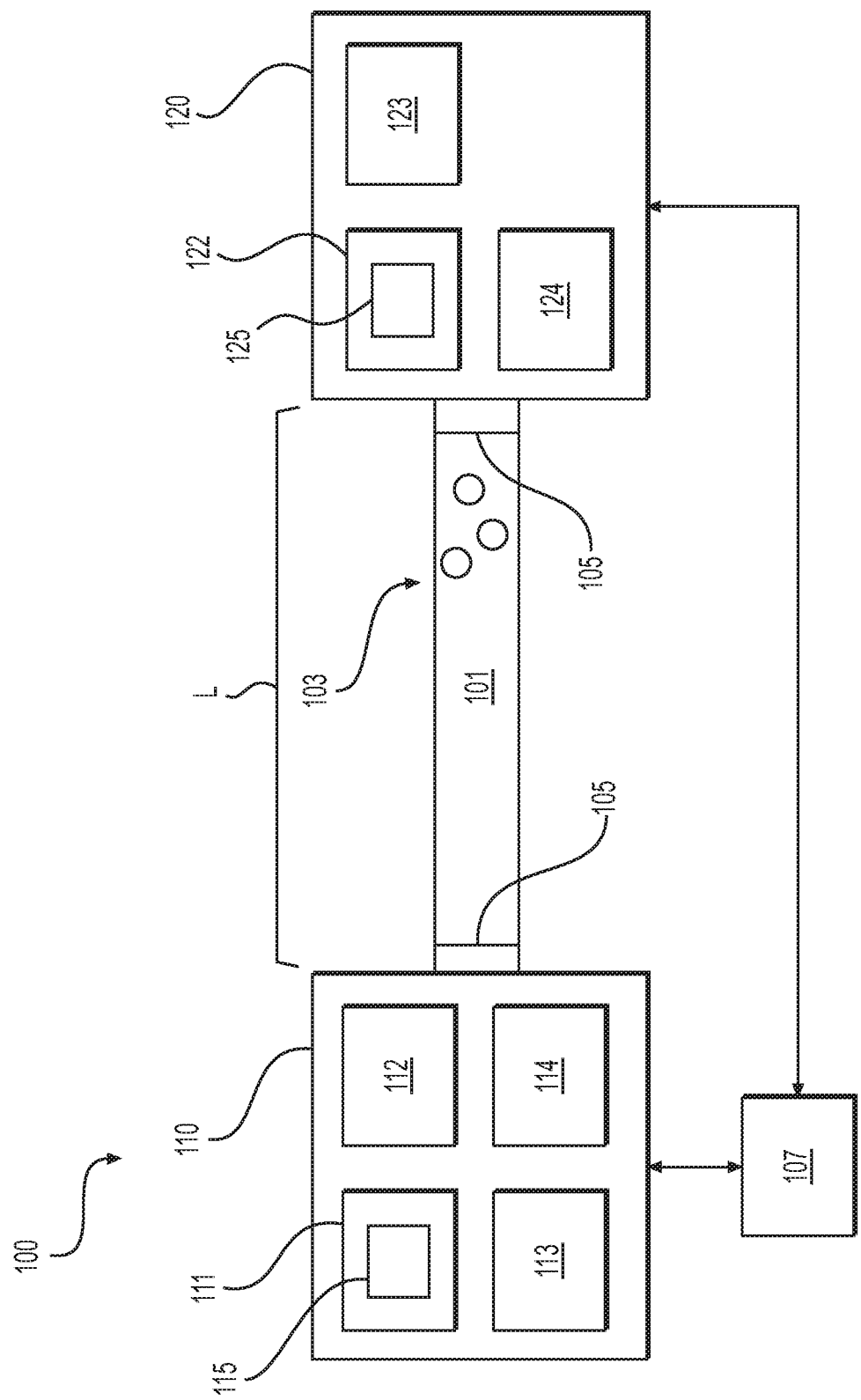
FIGS. 1A and B show schematic views of a terahertz spectroscopy device, according to one or more embodiments.

FIGS. 1A and B show schematic views of a terahertz spectroscopy device 100 used to identify a parameter associated with a sample, according to one or more embodiments. As shown in FIG. 1A, the device 100 includes spectral instruments 110 and 120, a waveguide 101, and a processor 107. The spectral instruments 110 and 120 are interconnected between the waveguide 101 to measure the spectral response of a sample 103 therein. The sample 103 includes any fluid, solid, gas, or liquid. As an example, the sample 103 may include a hydrocarbon fluid or an asphaltene. The spectral instruments 110, 120 can include various components, such as a transmitter 111, receivers 112 and 122, pumps 113 and 123, and thermal elements 114 and 124. Although these components (111-114 and 122-124) are depicted as being integrated or included in the spectral instruments 110 and 120, it should be appreciated that any of these may be separate components in communication with the spectral instrument 110 and/or 120.

To produce a spectral response between EM radiation and the sample 103, the transmitter 111 emits EM radiation in a terahertz frequency band into the waveguide 101. The transmitter 111 can generate a broadband pulse of EM radiation, e.g., a pulse having a width of about 100 femtoseconds and frequency components between about 0.1 THz and 3 THz. The transmitter 111 can sweep frequencies with narrowband pulses, for example, by transmitting monochromatic pulses between about 0.1 THz and about 3 THz at a resolution of about 3 GHz. The transmitter 111 can include a first polarizer 115 (e.g., a polarizing filter) configured to linearly polarize the EM radiation emitted from the transmitter 111. It should be appreciated that the transmitter 111 can also transmit a continuous wave of EM radiation to produce the spectral response of the sample 103, in addition, or as an alternative, to the pulses of EM radiation.

The waveguide 101 includes any suitable conduit to propagate EM radiation from one location to another location and to house the sample 103. As a non-limiting example, the waveguide 101 may be a conductive tubular to propagate the EM radiation from the transmitter 111 to the receiver 122 and/or from the transmitter 111 to the receiver 111, as further described herein. The waveguide 101 may be an overmoded waveguide with a circular cross-section. An overmoded waveguide is especially efficient for EM radiation traveling in a circular $TE_{01}$ mode through the waveguide. As used herein, an overmoded waveguide refers to a waveguide having an inner diameter larger than the minimum diameter required to allow the respective mode (e.g., $TE_{01}$) to propagate through the waveguide. For example, the waveguide 101 may be a tubular comprising a steel or copper alloy with a length L of about 10 meters and a diameter of about 1.3 centimeter (0.5 inches). Windows 105 that are transparent to terahertz EM radiation may be located on the ends of the waveguide 101 to house the sample 103 therein.

As used herein, the radiation path of the waveguide 101 refers to the path the EM radiation travels in the waveguide 101. The waveguide 101 can have a radiation path that attenuates the EM radiation caused from the interaction between the EM radiation and the sample 103. For example, a radiation path of at least 10 meters increases the waveguide's 101 volume that can be filled with the sample 103, which in turns increases the interaction between the sample 103 and the EM radiation, with respect to spectroscopy devices with radiation paths of a few centimeters. With a radiation path of at least 10 meters, the spectroscopy device 100 can be filled with an amount of the sample 103 that attenuates the EM radiation and produces detectable spectral parameters associated with the sample 103. The waveguide 101 can have a length L so that even if the interaction between the sample 103 and the EM radiation is weak, an absorption spectrum is detectable by the receiver 122. For example, the waveguide 101 can have a length L of 100 meters to increase the amount of the sample 103 housed in the waveguide, and thus, increase the interaction between the EM radiation and the sample 103.

Figure 1B:
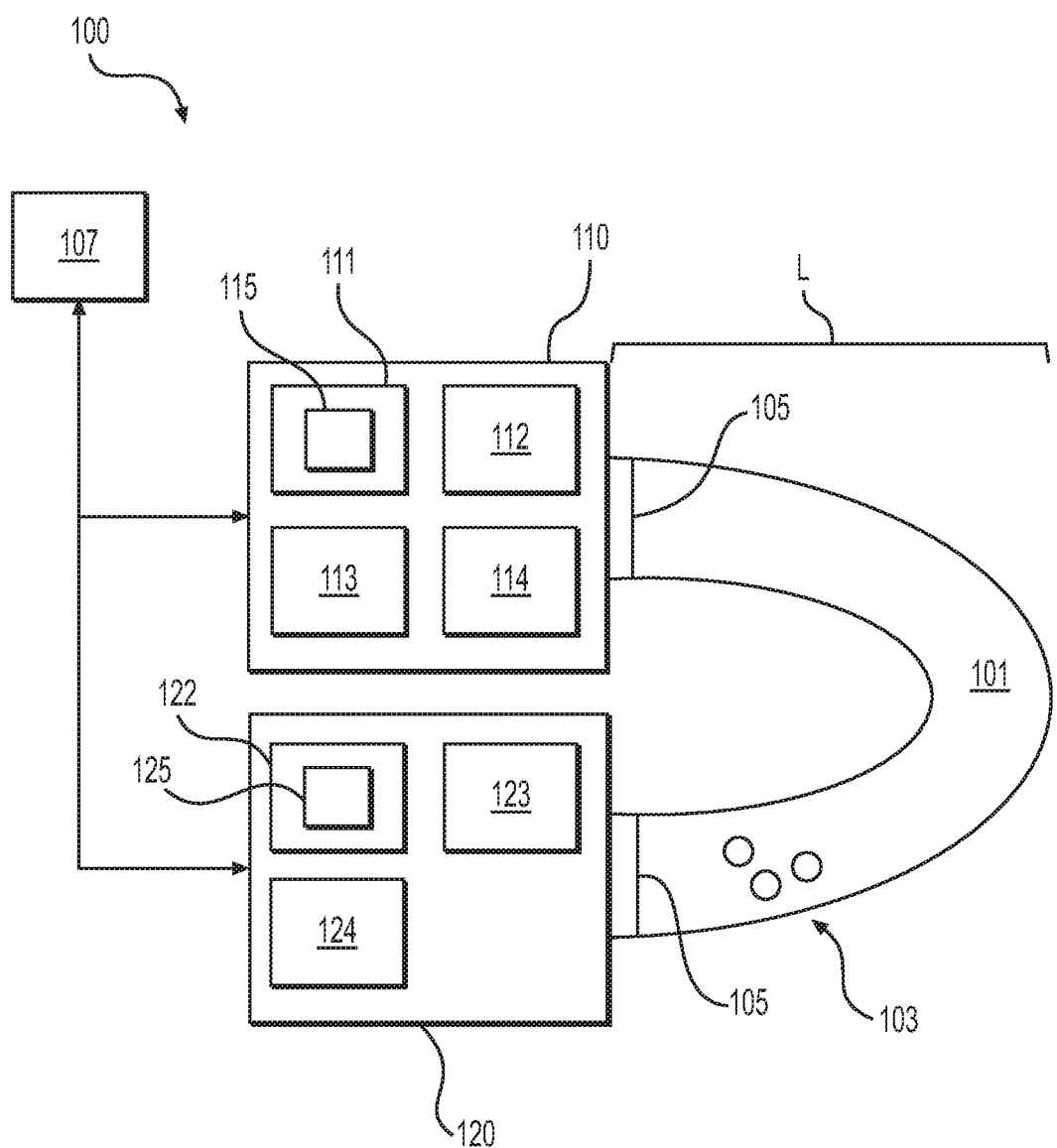

The radiation path can be effectively increased by including windows 105 that are at least partially reflective such that the EM radiation reflects back and forth within the waveguide 101 between the windows 105. For example, the length L may be about 5 meters with the EM radiation traveling effectively in average at least two lengths of the waveguide 101 between the reflective windows 105 for an effective length of at least 10 meters. Alternatively or additionally, as shown in FIG. 1B, the waveguide 101 may be folded to maintain a radiation path that increases the interaction between EM radiation and the sample 103, while making the spectroscopy system 100 relatively compact.

In one or more embodiments, the interaction between the EM radiation and the sample 103 may be controlled by the density of the sample 103. For example, the pumps 113 and 123 may increase the density of the sample 103 by applying pressure in the waveguide 101 such that the sample 103 is pressurized. This increased density increases the attenuation of the EM radiation caused from the interaction between the EM radiation and the sample 103 to improve the spectral analysis of the sample 103. Thus, it should be appreciated that the interaction between the EM radiation and the sample 103 may depend in part on the radiation path of the waveguide and/or the density of the sample 103.

The receiver 122 is in communication with the waveguide 101 and generates a signal in response to the EM radiation propagating through the waveguide 101 that is received by the receiver 122. The receiver 122 can include a second polarizer 125 (e.g., a polarizing filter) configured to rotate about the longitudinal axis of the waveguide 101 to identify the rotation angle of the received EM radiation induced by the sample 103. For example, the sample 103 can induce a rotation of the EM radiation propagating through the waveguide 101. The receiver 122 can rotate the second polarizer 125 until the maximum intensity of EM radiation incident to the second polarizer 125 passes through the second polarizer 125 and radiates onto the receiver 122 to generate a signal indicative of the EM radiation. With the transmitted EM radiation linearly polarized using the first polarizer 115, the rotation angle of the second polarizer 125 can be compared to the polarization angle of the transmitted EM radiation to identify the rotation angle of the EM radiation induced by the sample 103 as further described herein.

A processor 107 analyzes the signal to identify a parameter associated with the sample 103 based on spectroscopic principles and/or polarimetry principles. The parameter associated with the sample 103 can include at least one of a resonant frequency of the sample, an absorption coefficient of the sample, a concentration of the sample, a molecular weight of the sample, a density of the sample, a temperature of the sample, a chemical composition of the sample, chirality of the sample, a specific rotation of the sample, the presence of water in the sample, and the presence of a hydrocarbon in the sample. It should be appreciated that the parameter associated with the sample 103 may be identified by applying Beer's law, which relates the absorption of EM radiation to the properties of the material (e.g., the sample 103) through which the EM radiation is traveling.

The parameter associated with the sample 103 may be identified by applying principles of polarimetry to identify the specific rotation of the sample 103 and/or the chirality of the sample 103. For example, the processor 107 is configured to identify the rotation angle of the received EM radiation relative to the polarization angle induced by the first polarizer 115 by identifying the rotation angle of the second polarizer 125 that allows the maximum intensity of EM radiation to pass through the second polarizer 125. As used herein, the rotation angle of the received EM radiation refers to the polarization angle of the EM radiation relative to the linearly polarized EM radiation emitted from the transmitter 111 using the first polarizer 115.

In one or more embodiments, the receiver 112 generates a signal in response to backscatter EM radiation propagating through the waveguide 101. For example, the sample 103 may produce Rayleigh scattering in response to encountering the EM radiation emitted from the transmitter 111. In general, EM radiation reflects off the sample 103 back to the receiver 112, producing backscatter EM radiation. The processor 107 analyzes the signal indicative of the backscatter EM radiation to identify a parameter associated with the sample 103 as described herein.

The control and processing of the signals generated by the receivers 112 and 122 is performed with the use of a computer program on a suitable non-transitory machine readable storage medium, which may include ROM, EPROM, EEPROM, flash memory, a hard disk, a solid state disk, an optical disk, or a combination thereof. As used herein, the term processor is intended to include devices such as a field programmable gate array (FPGA). The results of the processing may be output to a suitable medium and/or may be used for identifying a parameter associated with the sample 103 as described herein.

In one or more embodiments, the pump 113 can generate a vacuum in the waveguide 101 before the sample 103 is injected into the waveguide 101 to analyze liquid samples in their gaseous phase. The pump 123 may inject the sample 103 into the waveguide 101 so that the sample 103 evaporates into the gaseous phase and a parameter associated with the sample 103 in its gaseous phase can be measured. Performing spectroscopy on a gaseous sample instead of a liquid sample can avoid the line-broadening in the spectral measurements observed in liquid samples, which in turn makes it difficult to identify individual resonances in liquid samples.

Time-resolved signals may be generated by the receivers 112 and 122 to recover information about the sample 103 based on the molecular weight of its constituent molecules. When the sample 103 is injected into the vacuum of the waveguide 101, lighter molecules within the sample 103 may evaporate faster than heavier molecules in the sample 103. This means if signals are generated by the receivers 112 and 122 after injecting the sample 103 into the waveguide 101, parameters associated with relatively light molecules in the sample 103 can be identified. At a later time, the heavier molecules evaporate so that the spectroscopy analysis generated at this later time is indicative of all the molecules in the sample 103. Thus, time-resolved measurements can provide a spectral analysis of molecules in the sample with different molecular weights, with the earlier time representative of relatively light molecules and the later time representative of all the molecules in the sample.

The pump 123 may inject the sample 103 into the waveguide 101 before a vacuum is created therein. As the pump 113 creates a vacuum in the waveguide 101, a pressure differential is developed, which in turn causes the lighter molecules to evaporate faster than the heavier molecules in the sample 103. Parameters associated with the relatively light molecules can be identified if the spectral analysis is performed as these light molecules evaporate. At a later time, parameters associated with the relatively heavy molecules can be identified because by the time the heavy molecules evaporate, the lighter molecules are removed from the waveguide 101 as the pump 113 continues to create the vacuum in the waveguide 101.

The thermal element 114 can generate a temperature differential across the waveguide 101 to analyze the diffusion properties of the sample 103. For example, the thermal element 113 can cool one end of the waveguide 101 when the sample 103 is injected by the pump 123 into the other end such that the sample 103 freezes as it diffuses to the cooler end of the waveguide 101. Additionally, or alternatively, the thermal element 124 can heat the waveguide 101 to provide a spectral analysis of the diffusion of the sample in the waveguide 101. With the diffusion properties of the sample 101, the molecular weight of the sample 103 can be identified, as it should be appreciated that the diffusion coefficient of a gas is inversely proportional to the molecular mass of that gas.

Figure 2:
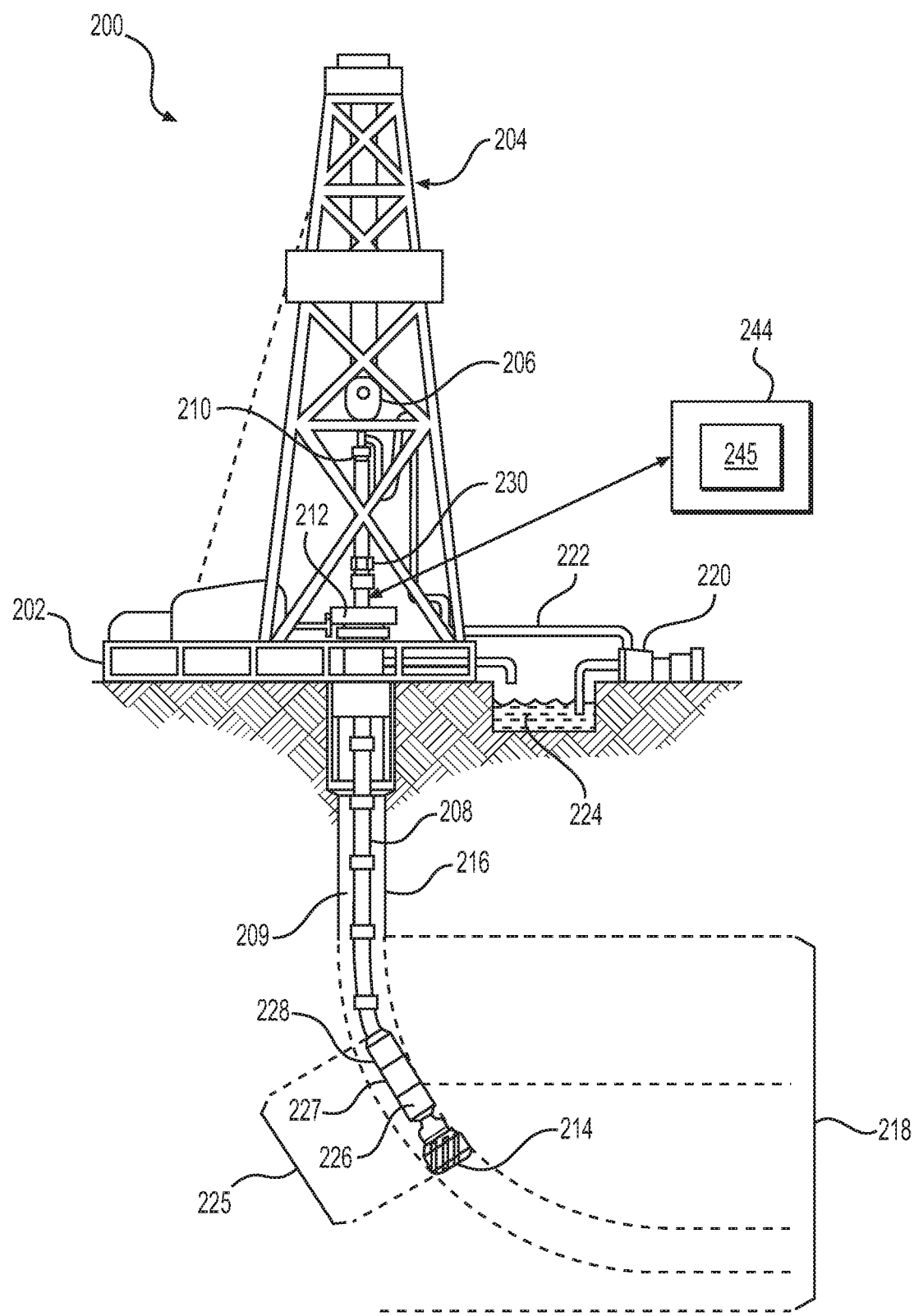
FIG. 2 shows a schematic view of a drilling environment, according to one or more embodiments.

FIG. 2 shows a schematic view a drilling operation employing a terahertz spectroscopy system 200, according to one or more embodiments. As shown, a drilling platform 202 supports a derrick 204 having a traveling block 206 for raising and lowering a drill string 208. A drill string kelly 210 supports the rest of the drill string 208 as it is lowered through a rotary table 212. The rotary table 212 rotates the drill string 208, thereby turning a drill bit 214. As the drill bit 214 rotates, it creates a wellbore 216 that passes through various subterranean earth formations 218. A pump 220 circulates drilling fluid through a feed pipe 222 to the kelly 210, downhole through the interior of the drill string 208, through orifices in the drill bit 214, back to the surface via an annulus 209 around the drill string 208, and into a retention pit 224. The drilling fluid transports cuttings from the wellbore 216 into the pit 224 and aids in maintaining the integrity of the wellbore 216.

A bottomhole assembly 225 is connected along the drill string 208 and includes drill collars 226, a downhole tool 227, and the drill bit 214. The drill collars 226 are thick-walled steel pipe sections that provide weight and rigidity for the drilling process. The downhole tool 227 (which may be built into one of the drill collars) may collect measurements relating to various wellbore and formation properties as well as the position of the bit 214 and various other drilling conditions as the bit 214 extends the wellbore 216 through the formations 218. For example, the downhole tool 227 includes a terahertz spectroscopy device 228 in accordance with one or more embodiments to identify a parameter associated with fluid samples collected from the formations 218, such as identifying the presence of asphaltenes, water, or a hydrocarbon fluid.

In one or more embodiments, the downhole tool 227 may include a device for measuring formation resistivity, a gamma ray device for measuring formation gamma ray intensity, devices for measuring the inclination and azimuth of the tool string 208, pressure sensors for measuring drilling fluid pressure, temperature sensors for measuring wellbore temperature, etc. The downhole tool 227 may also include a telemetry module that receives data provided by the various sensors of the bottomhole assembly 225 (e.g., the terahertz spectroscopy device 228), and transmits the data to a surface control unit 244. Data may also be provided by the surface control unit 244, received by the telemetry module, and transmitted to the sensors (e.g., the terahertz spectroscopy device 228) of the bottomhole assembly 225. The surface control unit 244 includes a computer system 245 for processing and storing the measurements gathered by the sensors. The computer system 245 may also be capable of controlling the bottomhole assembly 225. Among other things, the computer system 245 may include a processor and a non-transitory computer-readable medium (e.g., a hard-disk drive and/or memory) capable of executing instructions to perform such tasks.

Figure 3:
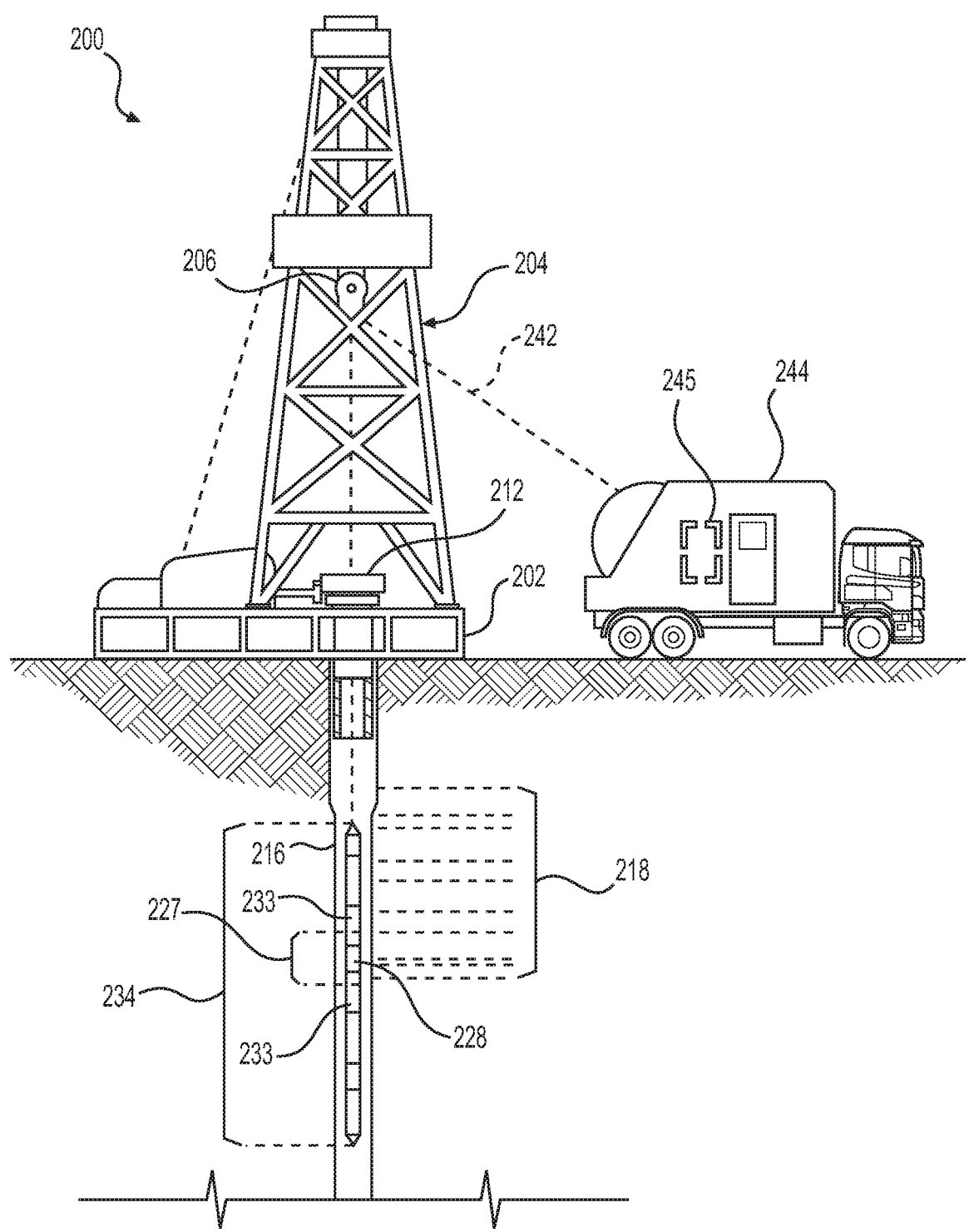
FIG. 3 shows a schematic view of a wireline logging environment, according to one or more embodiments.

FIG. 3 shows a schematic view of a wireline logging environment in which the terahertz spectroscopy device 228, in accordance with one or more embodiments described in the present disclosure, may be used. As shown, logging operations can be conducted using a wireline logging string 234, e.g., a wireline logging sonde, suspended by a cable 242 that communicates power to the logging string 234 and telemetry signals between the logging string 234 and the surface. The logging string 234 includes the downhole tool 227, which may obtain terahertz spectroscopy measurements as described herein. For example, the terahertz spectroscopy device 228 may identify a parameter associated with a sample collected as a function of depth in the wellbore 216 as described herein.

The downhole tool 227 may be coupled to other modules of the wireline logging string 234 by one or more adaptors 233. The surface control unit 244 collects measurements from the logging string 234 for processing and storing the measurements gathered by the sensors. In addition to collecting and processing measurements, the computer system 245 may be capable of controlling the logging string 234 and downhole tool 227. The surface control unit 244 may further include a user interface (not shown) which displays the measurements, for example, a monitor or printer.

Figure 4:
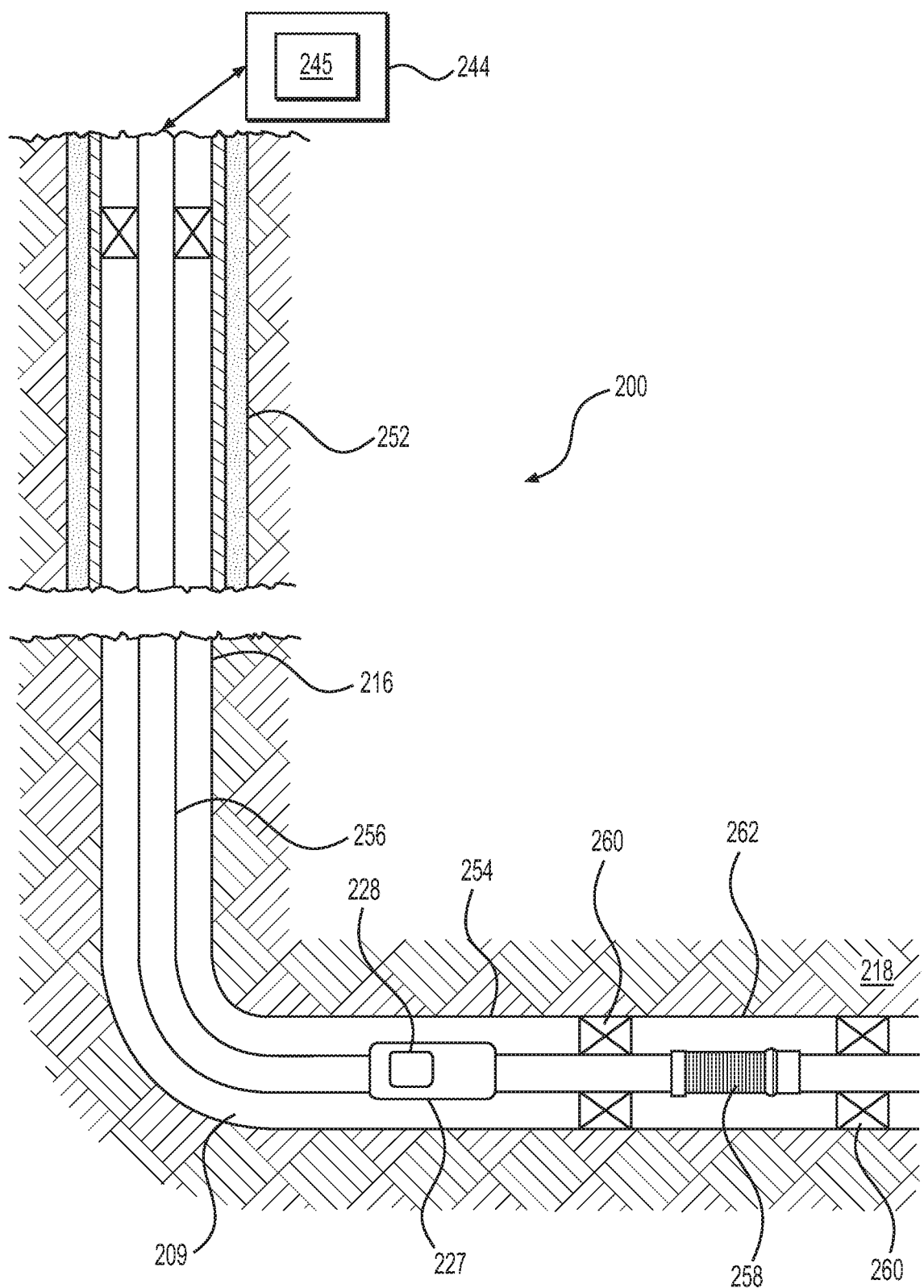
FIG. 4 shows a schematic view of a production and/or completion environment, according to one or more embodiments.

FIG. 4 shows a schematic view of the terahertz device 228 employed in a completion and/or production environment, in accordance with one or more embodiments. As shown, the wellbore 216 is at least partially cemented with a casing string 252 and also has an open-hole section 254. Positioned within the wellbore 216 and extending from the surface is a tubing string 256, which provides a conduit for formation fluids to travel from the formation 218 to the surface and for stimulation fluids to travel from the surface to the formation 218. The tubing string 256 includes a flow control device 258, which is positioned between a pair of annular barriers depicted as packers 260 that provide a fluid seal between the tubing string 256 and the wellbore 216, thereby defining a production and/or stimulation interval 262. The flow control devices 258 are employed to filter particulate matter out of the production fluid stream from the formation 218 or inject stimulation fluid into the formation 218. Positioned in the wellbore 216 is the downhole tool 227, which may obtain terahertz spectroscopy measurements as described herein. For example, the terahertz spectroscopy device 228 may be in fluid communication with the tubing string 256 and/or the annulus 209 to identify a parameter associated with a fluid sample taken from the tubing string 256 and/or the annulus 209 as further described herein. Thus, it should be appreciated that the terahertz spectroscopy device 228 may be used in various applications, such as wireline, slickline, coiled tubing, MWD, LWD, production tubing, flowline, hydrocarbon processing, hydrocarbon separation, etc.

In addition to the embodiments described above, many examples of specific combinations are within the scope of the disclosure, some of which are detailed below:

Example 1

A device for analyzing a sample, comprising:
a transmitter configured to generate electromagnetic (EM) radiation in a terahertz frequency band from about 0.1 terahertz to about 10 terahertz;
a waveguide configured to propagate the EM radiation generated from the transmitter and house the sample to attenuate the EM radiation;
a receiver in communication with the waveguide and configured to generate a signal in response to EM radiation propagating in the waveguide; and
a processor configured to analyze the signal to identify a parameter associated with the sample.

Example 2

The device of example 1, wherein the parameter associated with the sample includes at least one of resonant frequency, absorption coefficient, concentration, molecular weight, density, temperature, chemical composition, chirality, specific rotation, the presence of water in the sample, and the presence of a hydrocarbon in the sample.

Example 3

The device of example 1, wherein the transmitter is configured to generate EM radiation across a spectrum of frequencies.

Example 4

The device of example 1, wherein the transmitter is configured to sweep frequencies of EM radiation.

Example 5

The device of example 1, wherein the transmitter comprises a first polarizer configured to linearly polarize the EM radiation generated from the transmitter, and the receiver comprises a second polarizer configured to rotate to identify a rotation angle of the EM radiation.

Example 6

The device of example 1, further comprising a pump to create a vacuum in the waveguide such that the sample is evaporable in the waveguide.

Example 7

The device of example 1, further comprising a thermal element to generate a temperature differential across the waveguide.

Example 8

The device of example 1, further comprising:
a second receiver in communication with the opposite end of the waveguide as the receiver and configured to generate a second signal in response to backscatter EM radiation propagating through the waveguide; and
wherein the processor is further configured to analyze the second signal to identify an additional parameter associated with the sample.

Example 9

The device of example 1, further comprising a pump configured to pressurize the sample in the waveguide to increase the density of the sample.

Example 10

The device of example 1, wherein the sample comprises an asphaltene.

Example 11

A method of analyzing a sample, comprising:
transmitting electromagnetic (EM) radiation in a terahertz frequency band from about 0.1 terahertz to about 10 terahertz using a transmitter through a waveguide with the sample therein to attenuate the EM radiation;
receiving the EM radiation propagating through the waveguide using a receiver to generate a signal in response to the received EM radiation; and
analyzing the signal to identify a parameter associated with the sample.

Example 12

The method of example 11, wherein the transmitting comprises transmitting the EM radiation across a spectrum of frequencies.

Example 13

The method of example 11, wherein the transmitting comprises sweeping frequencies of EM radiation.

Example 14

The method of example 11, further comprising creating a vacuum in the waveguide to evaporate the sample.

Example 15

The method of example 11, further comprising generating a temperature differential across the waveguide.

Example 16

The method of example 11, further comprising:
receiving backscatter EM radiation propagating through the waveguide;
generating a second signal in response to the backscatter EM radiation;
analyzing the second signal to identify an additional parameter associated with the sample.

Example 17

The method of example 11, wherein the parameter associated with the sample includes at least one of resonant frequency, absorption coefficient, concentration, molecular weight, density, temperature, chemical composition, chirality, specific rotation, the presence of water in the sample, and the presence of a hydrocarbon in the sample.

Example 18

The method of example 11, wherein the sample comprises an asphaltene.

Example 19

The method of example 14, wherein:
transmitting EM radiation comprises transmitting EM radiation at a first time and a second time;
receiving EM radiation comprises receiving EM radiation propagating from the first time to generate a first signal and receiving EM radiation from the second time to generate a second signal; and
analyzing comprises analyzing the first signal and the second signal to identify a parameter associated with molecules with different molecular weights in the sample.

Example 20

The method of example 11, wherein:
transmitting EM radiation comprises linearly polarizing the EM radiation at a polarization angle using a first polarizer; and
receiving EM radiation comprises rotating a second polarizer to identify a rotation angle of the EM radiation relative to the polarization angle.

Example 21

A system for analyzing a sample located in a wellbore intersecting a subterranean earth formation, comprising:
a downhole tool locatable in a wellbore and comprising:
a transmitter configured to generate electromagnetic (EM) radiation in a terahertz frequency band from about 0.1 terahertz to about 10 terahertz;
a waveguide configured to propagate the EM radiation generated from the transmitter and house the sample to attenuate the EM radiation; and
a receiver in communication with the waveguide and configured to generate a signal in response to EM radiation propagating in the waveguide; and
a processor configured to analyze the signal to identify a parameter associated with the sample.

Example 22

The system of example 20, further comprising a pump coupled to the waveguide to create a vacuum in the waveguide such that the sample is evaporable in the waveguide.

Example 23

The system of example 20, further comprising a thermal element coupled to the waveguide to generate a temperature differential across the waveguide.

Example 24

The system of example 20, wherein the sample comprises an asphaltene.

This discussion is directed to various embodiments. The drawing figures are not necessarily to scale. Certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed may be employed separately or in any suitable combination to produce desired results. In addition, one skilled in the art will understand that the description has broad application, and the discussion of any embodiment is meant only to be exemplary of that embodiment, and not intended to suggest that the scope of the disclosure, including the claims, is limited to that embodiment.

Certain terms are used throughout the description and claims to refer to particular features or components. As one skilled in the art will appreciate, different persons may refer to the same feature or component by different names. This document does not intend to distinguish between components or features that differ in name but not function, unless specifically stated. In the discussion and in the claims, the terms "including" and "comprising" are used in an open-ended fashion, and thus should be interpreted to mean "including, but not limited to . . . ." Also, the term "couple" or "couples" is intended to mean either an indirect or direct connection. In addition, the terms "axial" and "axially" generally mean along or parallel to a central axis (e.g., central axis of a body or a port), while the terms "radial" and "radially" generally mean perpendicular to the central axis. The use of "top," "bottom," "above," "below," and variations of these terms is made for convenience, but does not require any particular orientation of the components.

Reference throughout this specification to "one embodiment," "an embodiment," or similar language means that a particular feature, structure, or characteristic described in connection with the embodiment may be included in at least one embodiment of the present disclosure. Thus, appearances of the phrases "in one embodiment," "in an embodiment," and similar language throughout this specification may, but do not necessarily, all refer to the same embodiment.

Although the present disclosure has been described with respect to specific details, it is not intended that such details should be regarded as limitations on the scope of the disclosure, except to the extent that they are included in the accompanying claims.

What is claimed is:

1. A device for analyzing a sample, comprising:
a transmitter configured to generate electromagnetic (EM) radiation in a terahertz frequency band from about 0.1 terahertz to about 10 terahertz;
a waveguide configured to propagate the EM radiation generated from the transmitter and house the sample to attenuate the EM radiation;
a receiver in communication with the waveguide and configured to generate a signal in response to EM radiation propagating in the waveguide; and
a processor configured to analyze the signal to identify a parameter associated with the sample.

2. The device of claim 1, wherein the parameter associated with the sample includes at least one of resonant frequency, absorption coefficient, concentration, molecular weight, density, temperature, chemical composition, chirality, specific rotation, the presence of water in the sample, and the presence of a hydrocarbon in the sample.

3. The device of claim 1, wherein the transmitter is configured to generate EM radiation across a spectrum of frequencies.

4. The device of claim 1, wherein the transmitter is configured to sweep frequencies of EM radiation.

5. The device of claim 1, wherein the transmitter comprises a first polarizer configured to linearly polarize the EM radiation generated from the transmitter, and the receiver comprises a second polarizer configured to rotate to identify a rotation angle of the EM radiation.

6. The device of claim 1, further comprising a pump to create a vacuum in the waveguide such that the sample is evaporable in the waveguide.

7. The device of claim 1, further comprising a thermal element to generate a temperature differential across the waveguide.

8. The device of claim 1, further comprising:
a second receiver in communication with the opposite end of the waveguide as the receiver and configured to generate a second signal in response to backscatter EM radiation propagating through the waveguide; and
wherein the processor is further configured to analyze the second signal to identify an additional parameter associated with the sample.

9. The device of claim 1, further comprising a pump configured to pressurize the sample in the waveguide to increase the density of the sample.

10. The device of claim 1, wherein the sample comprises an asphaltene.

11. A method of analyzing a sample, comprising:
transmitting electromagnetic (EM) radiation in a terahertz frequency band from about 0.1 terahertz to about 10 terahertz using a transmitter through a waveguide with the sample therein to attenuate the EM radiation;
receiving the EM radiation propagating through the waveguide using a receiver to generate a signal in response to the received EM radiation; and
analyzing the signal to identify a parameter associated with the sample.

12. The method of claim 11, wherein the transmitting comprises transmitting the EM radiation across a spectrum of frequencies.

13. The method of claim 11, wherein the transmitting comprises sweeping frequencies of EM radiation.

14. The method of claim 11, further comprising creating a vacuum in the waveguide to evaporate the sample.

15. The method of claim 11, further comprising generating a temperature differential across the waveguide.

16. The method of claim 11, further comprising:
receiving backscatter EM radiation propagating through the waveguide;
generating a second signal in response to the backscatter EM radiation;
analyzing the second signal to identify an additional parameter associated with the sample.

17. The method of claim 11, wherein the parameter associated with the sample includes at least one of resonant frequency, absorption coefficient, concentration, molecular weight, density, temperature, chemical composition, chirality, specific rotation, the presence of water in the sample, and the presence of a hydrocarbon in the sample.

18. The method of claim 11, wherein the sample comprises an asphaltene.

19. The method of claim 14, wherein:
transmitting EM radiation comprises transmitting EM radiation at a first time and a second time;
receiving EM radiation comprises receiving EM radiation propagating from the first time to generate a first signal and receiving EM radiation from the second time to generate a second signal; and
analyzing comprises analyzing the first signal and the second signal to identify a parameter associated with molecules with different molecular weights in the sample.

20. The method of claim 11, wherein:
transmitting EM radiation comprises linearly polarizing the EM radiation at a polarization angle using a first polarizer; and
receiving EM radiation comprises rotating a second polarizer to identify a rotation angle of the EM radiation relative to the polarization angle.

21. A system for analyzing a sample located in a wellbore intersecting a subterranean earth formation, comprising:
a downhole tool locatable in a wellbore and comprising:
a transmitter configured to generate electromagnetic (EM) radiation in a terahertz frequency band from about 0.1 terahertz to about 10 terahertz;
a waveguide configured to propagate the EM radiation generated from the transmitter and house the sample to attenuate the EM radiation; and
a receiver in communication with the waveguide and configured to generate a signal in response to EM radiation propagating in the waveguide; and
a processor configured to analyze the signal to identify a parameter associated with the sample.

22. The system of claim 20, further comprising a pump coupled to the waveguide to create a vacuum in the waveguide such that the sample is evaporable in the waveguide.

23. The system of claim 20, further comprising a thermal element coupled to the waveguide to generate a temperature differential across the waveguide.

24. The system of claim 20, wherein the sample comprises an asphaltene.

* * * * *